(12) United States Patent
Wakayama

(10) Patent No.: US 8,247,601 B2
(45) Date of Patent: Aug. 21, 2012

(54) 2-ACRYLAMIDE-2-METHYLPROPANESULFONIC ACID AND PROCESS FOR PRODUCING THE SAME

(75) Inventor: Toshiyuki Wakayama, Nagoya (JP)

(73) Assignee: Toagosei Co., Ltd., Tokyo (JP)

( * ) Notice: Subject to any disclaimer, the term of this patent is extended or adjusted under 35 U.S.C. 154(b) by 207 days.

(21) Appl. No.: 12/746,124

(22) PCT Filed: Dec. 2, 2008

(86) PCT No.: PCT/JP2008/071845
§ 371 (c)(1),
(2), (4) Date: Jun. 3, 2010

(87) PCT Pub. No.: WO2009/072480
PCT Pub. Date: Jun. 11, 2009

(65) Prior Publication Data
US 2010/0274048 A1    Oct. 28, 2010

(30) Foreign Application Priority Data

Dec. 6, 2007 (JP) ................................. 2007-315989
Dec. 19, 2007 (JP) ................................. 2007-326810
Jan. 8, 2008 (JP) ................................. 2008-001236

(51) Int. Cl.
*C07C 309/00* (2006.01)

(52) U.S. Cl. .................................................... 562/105
(58) Field of Classification Search .................. 562/105
See application file for complete search history.

(56) References Cited

FOREIGN PATENT DOCUMENTS

| JP | 1975-030059 B | 9/1975 |
|---|---|---|
| JP | 2003-137857 A | 5/2003 |
| JP | 2004-143078 A | 5/2004 |
| JP | 2004-277363 A | 10/2004 |
| JP | 2004-359591 A | 12/2004 |

*Primary Examiner* — Porfirio Nazario Gonzalez
(74) *Attorney, Agent, or Firm* — Norris McLaughlin & Marcus PA

(57) ABSTRACT

A process for producing 2-acrylamide-2-methyl propane sulfonic acid (ATBS) which comprises reacting acrylonitrile, fuming sulfuric acid, and isobutylene. During the reaction, the concentration of 2-methyl-2-propenyl-1-sulfonic acid (IBSA) and/or that of 2-methylidene-1,3-propylenedisulfonic acid (IBDSA) in the reaction system are determined. When the IBSA concentration exceeds 12,000 mass ppm and/or the IBDSA concentration exceeds 6,000 mass ppm, then the concentration of sulfur trioxide in the reaction system is reduced. Thus, ATBS having an IBSA content of 100 mass ppm or lower and an IBDSA content of 100 mass ppm or lower is produced.

8 Claims, 4 Drawing Sheets

[Fig.1]
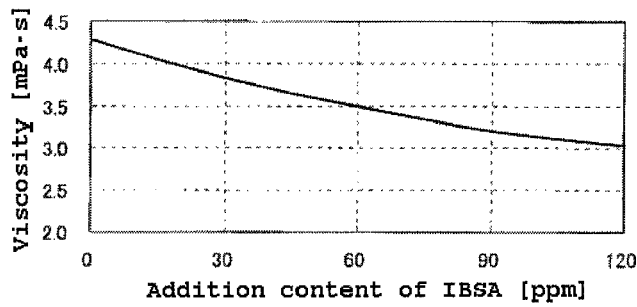
[Fig.2]
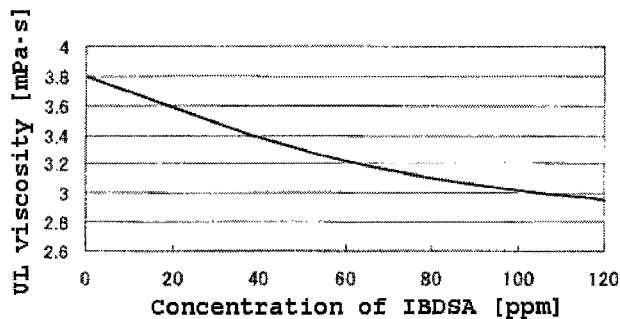
[Fig.3]
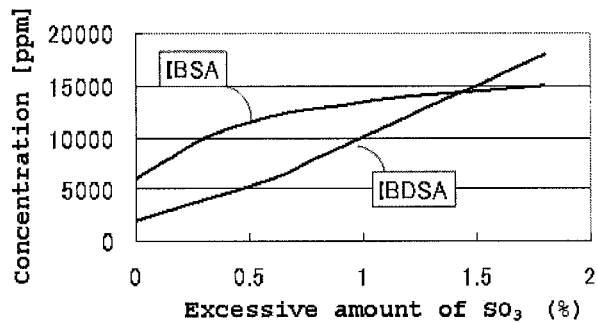
[Fig.4]
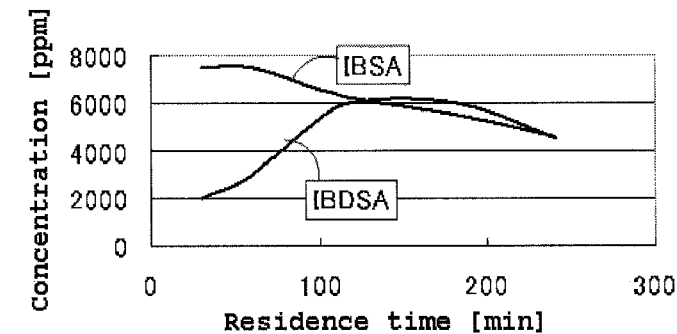

[Fig.5]
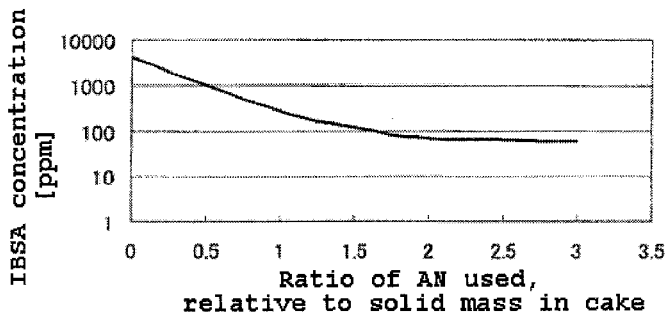
[Fig.6]
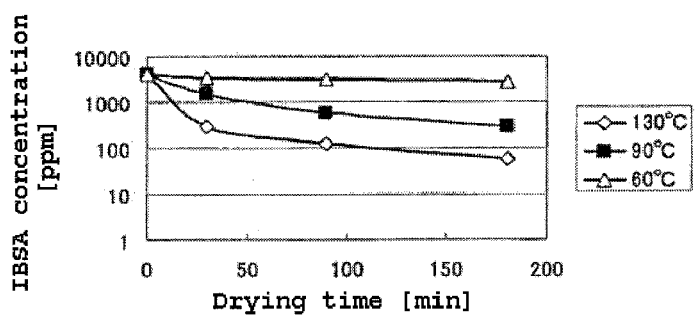
[Fig.7]
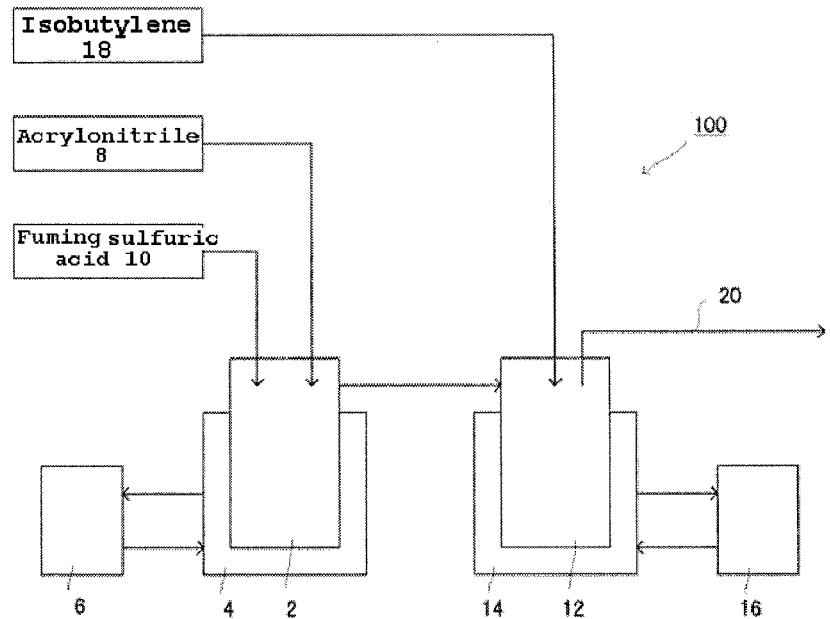

[Fig.8]
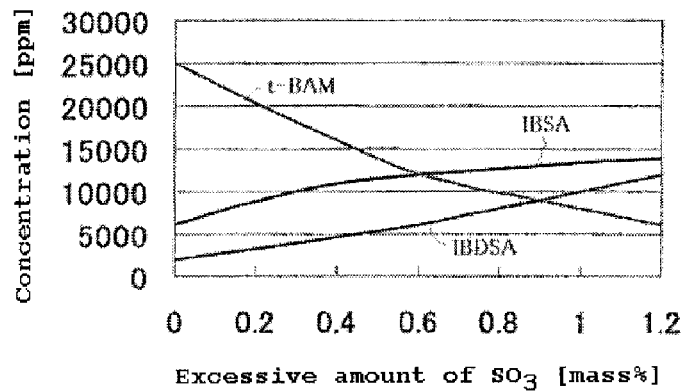
[Fig.9]
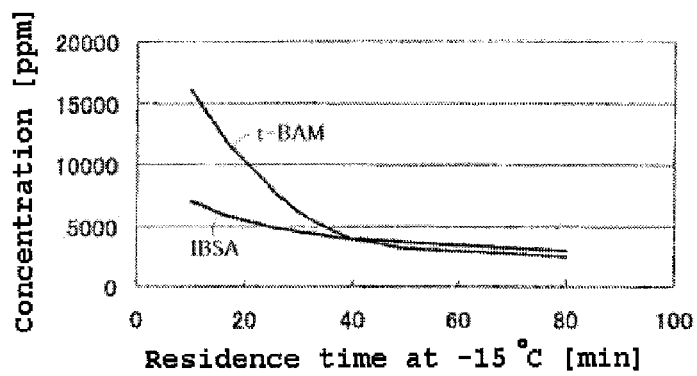
[Fig.10]
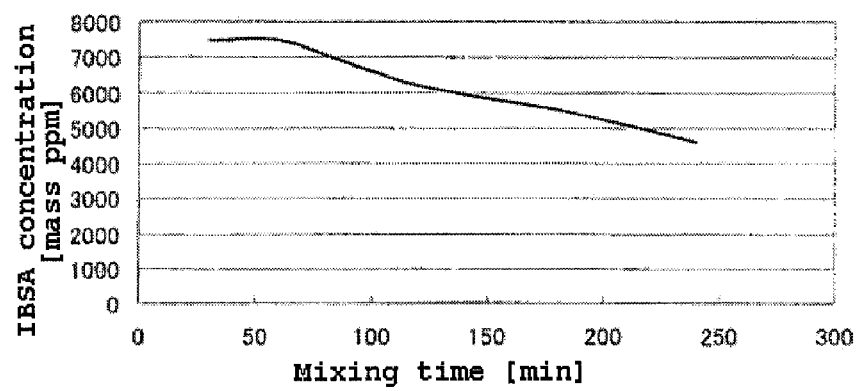

[Fig.11]
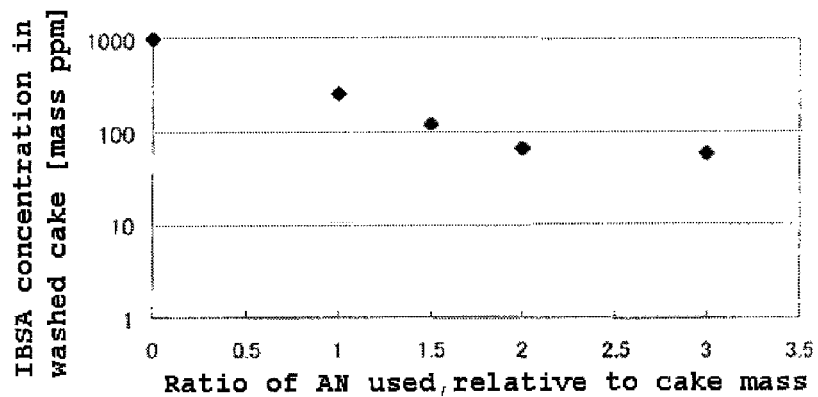
[Fig.12]
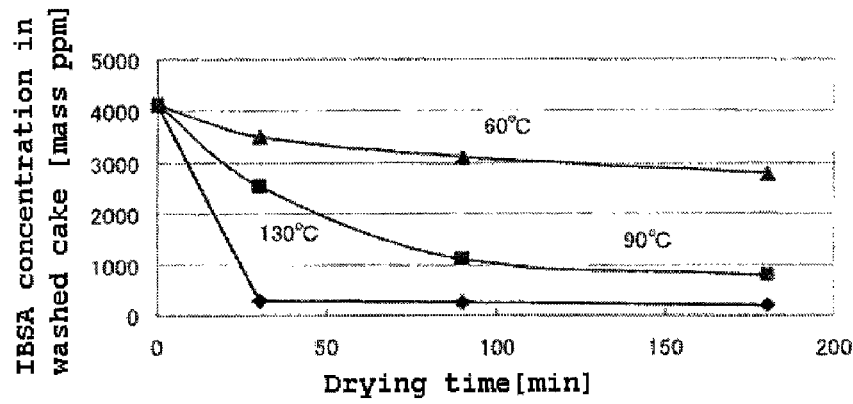

2-ACRYLAMIDE-2-METHYLPROPANESULFONIC ACID AND PROCESS FOR PRODUCING THE SAME

TECHNICAL FIELD

The present invention relates to 2-acrylamide-2-methylpropanesulfonic acid (hereinafter, this may be referred to as ATBS) and a process for producing the compound. More particularly, the present invention relates to ATBS low in content of particular impurities and a process for producing the compound.

BACKGROUND ART

ATBS is in use in wide fields, for example, as a modifier for acrylic fiber, a monomer raw material for dispersing agent or coagulating agent, a monomer raw material for thickening agent of cosmetic, or a monomer raw material for production of a chemical used in higher-order recovery of crude oil.

A polymer produced from the ATBS (raw material monomer) used in the above applications is required to have, in particular, a high molecular weight. Therefore, the ATBS used in the above applications need to be minimized in the content of substances hindering the polymerization and have stable quality.

ATBS is ordinarily produced by subjecting acrylonitrile, sulfuric acid and isobutylene to an addition reaction. ATBS is a white, needle-like crystal at a normal state and has a melting point of 185° C. (for example, Patent Literature 1).

In the above addition reaction, the tree components of acrylonitrile, sulfuric acid and isobutylene react at an equimolar ratio stoichiometrically. However, acrylonitrile is used ordinarily in a large excess relative to sulfuric acid and isobutylene, because acrylonitrile functions also as a reaction medium.

ATBS is insoluble in acrylonitrile. Therefore, the reaction product obtained by the reaction is in a slurry state in which ATBS separates out in acrylonitrile. In production of ATBS, it is ordinarily conducted to separate a crude ATBS from the slurry and then purify the crude ATBS in the next purification step.

The purification method includes a method of washing the crude ATBS with acrylonitrile (for example, Patent Literature 1).

There are also a method of recrystallizing the crude ATBS from methanol (for example, Patent Literature 2) and a method of purifying the crude ATBS using an anion exchange resin (for example, Patent Literature 3). Further, there is known, for example, a method of subjecting an aqueous solution of ATBS to distillation in the presence of acrylonitrile to remove water and obtain an acrylonitrile dispersion of ATBS and then separating ATBS from the dispersion by filtration (for example, Patent Literature 4).

However, the substances hindering the polymerization in ATBS have not been identified exactly. Therefore, the above needs have been satisfied by purifying ATBS sufficiently. This method of sufficient purification is not a special method for removing particular substances hindering the polymerization of ATBS, because such substances are not yet identified. There has been used simply a method ordinarily used for enhancement of purity. Therefore, there occurs, in some cases, excessive purification. As a result, the concentration of impurities in the ATBS obtained is unstable and varies each time.

Patent Literature 1: JP-B-1975-30059 (Example 1)
Patent Literature 2: JP-A-2004-359591 (Claim 1)
Patent Literature 3: JP-A-2004-143078 (Claim 1)
Patent Literature 4: JP-A-2004-277363 (Claim 1)

DISCLOSURE OF THE INVENTION

Technical Problem

The present inventor made various investigations in order to solve the above problems. As a result, the following matters were found.

Firstly, it was found that the reaction by-products, i.e. 2-methyl-2-propenyl-1-sulfonic acid (abbreviated as IBSA) represented by the following formula (1)

[Formula 1]

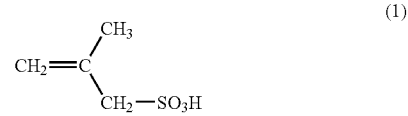

and 2-methylidene-1,3-propylenedisulfonic acid (abbreviated as IBDSA) represented by the following formula (2)

[Formula 2]

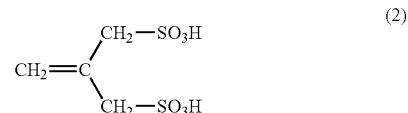

had a chain transfer action in polymerization.

It was found that an increase in these compounds in ATBS gave a copolymer of ATBS not large in molecular weight.

Further, it was confirmed that the contents of the above by-products could be accurately determined by high performance liquid chromatography. It was further learned that, by controlling the above by-products at levels not higher than particular values, in the production of ATBS, ATBS capable of producing a high-molecular weight polymer could be produced.

Accordingly, the first object of the present invention lies in providing ATBS low in the contents of compounds hindering the polymerization, and a process for production of such ATBS.

Secondly, the present inventor made various investigations to order to increase the yield of ATBS. As a result, it was learned that important points described below needed be considered in continuous production of ATBS by reaction of acrylonitrile, sulfuric acid and isobutylene.

(1) This reaction is an equimolar reaction of the three components of sulfuric acid, isobutylene and acrylonitrile and they react with each other to form ATBS.

(2) Meanwhile, the raw materials such as sulfuric acid, acrylonitrile and the like contain water fluctuating in amount, and accordingly the reaction conditions fluctuate. As a result, ATBS is not obtained quantitatively and, in some cases, tert-butylacrylamide and acrylamide are produced as by-products in large amounts.

(3) In order to solve this water problem, fuming sulfuric acid has been used in place of sulfuric acid. By reacting the sulfur trioxide ($SO_3$) in fuming sulfuric acid, with the water present in raw materials such as acrylonitrile and the like, the water in the raw materials is removed and water-free sulfuric acid is formed.

(4) However, when fuming sulfuric acid is added to the reaction system in an amount larger than required for the water removal, sulfur trioxide remains in the reaction system. In this case, sulfonation of isobutylene takes place as a side reaction, which forms 2-methyl-2-propenyl-1-sulfonic acid (IBSA) and 2-methylidene-1,3-propylenedisulfonic acid (IBDSA). In radical polymerization, these compounds showing a chain transfer action function as a molecular weight-controlling agent. When contained in ATBS produced, these compounds reduce the polymerizability of ATBS.

(5) In order to solve these problems, it is necessary to minimize the concentration of the sulfur trioxide remaining in the reaction system after water removal.

With attention being paid to these points, actual production of ATBS was conducted using a synthesis equipment described later. As a result, although there was formation of by-products, i.e. tert-BAM represented by the following formula (4),

[Formula 3]

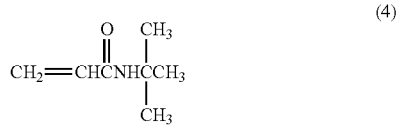

(4)

acrylamide, IBSA and IBDSA, their total amounts could be lowered. In this case, the reaction yield of ATBS was about 88% based on isobutylene.

However, in the above reaction, expensive isobutylene and acrylonitrile are consumed by the formation of the above-mentioned by-products. In order to produce ATBS inexpensively, it is necessary to suppress the side reactions and increase the yield of product.

Hence, the second object of the present invention lines in providing a process for producing ATBS at a high reaction yield.

Thirdly, the present inventor found as mentioned previously that the by-products, i.e. 2-methyl-2-propenyl-1-sulfonic acid (IBSA) and 2-methylidene-1,3-propylenedisulfonic acid (IBDSA) showed a chain transfer action in polymerization.

The present inventor found that a fluctuation particularly in IBSA content results in the fluctuation in the molecular weights of copolymer of ATBS and neutralization salt thereof, making it impossible to obtain a copolymer of stable quality.

The presence of these compounds is known. However, under what production conditions these compounds are formed in what amounts, is unknown.

The present inventor made an in-depth investigation on the behaviors of the above-mentioned IBSA and IBDSA in each step of the production of IBSA comprising a reaction step, a solid-liquid separation step, a solid purification step and a solid drying step.

In the investigation, first, there were examined the methods employable for quantitative determination of IBSA and IBDSA, using analytical instruments. As a result, it was confirmed that capillary electrophoresis, ion chromatography and high performance liquid chromatography (HPLC) were effective for the quantitative determination of the above compounds. It was found that HPLC was particularly effective and the compounds could be easily determined quantitatively by setting the analytical conditions of HPLC in detail.

Next, the content of IBSA in ATBS was determined quantitatively by HPLC. Further, a copolymer of the ATBS for which the content of IBSA was measured and other monomer was produced and a viscosity thereof was measured. As a result, it was found that, in order to produce a copolymer of ATBS having a larger molecular weight than conventional copolymer of ATBS does, the content of IBSA in ATBS was necessary to be 30 mass ppm or lower.

Accordingly, the object of the present invention lies in providing ATBS in which the content of IBSA hindering polymerization of ATBS is 30 mass ppm or lower, as well as a process for producing such ATBS.

Technical Solution

The present inventions achieving the above objects are as follows.

[1] 2-Acrylamide-2-methylpropanesulfonic acid represented by the following formula (3)

[Formula 4]

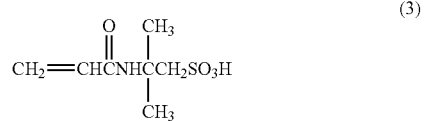

(3)

wherein the content of 2-methyl-2-propenyl-1-sulfonic acid represented by the following formula (1)

[Formula 5]

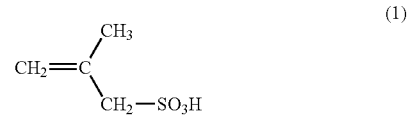

(1)

is 100 mass ppm or lower and the content of 2-methylidene-1,3-propylenedisulfonic acid represented by the following formula (2)

[Formula 6]

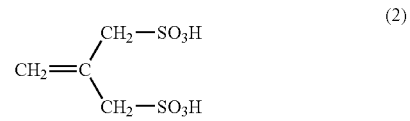

(2)

is 100 mass ppm or lower.

[2] 2-Acrylamide-2-methylpropanesulfonic acid according to claim 1, wherein the content of 2-methyl-2-propenyl-1-sulfonic acid represented by the following formula (1)

[Formula 7]

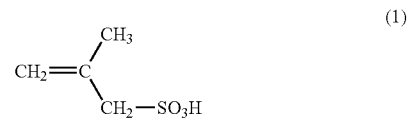

(1)

is 30 mass ppm or lower.

[3] A process for producing 2-acrylamide-2-methylpropanesulfonic acid, which comprises reacting acrylonitrile, fuming sulfuric acid and isobutylene, wherein the concentration of the 2-methyl-2-propenyl-1-sulfonic acid and/or 2-methylidene-1,3-propylenedisulfonic acid present in the reaction system is determined during the reaction and, when the concentration of 2-methyl-2-propenyl-1-sulfonic acid exceeds 12,000 mass ppm and/or the concentration of 2-methylidene-1,3-propylenedisulfonic acid exceeds 6,000 mass ppm, the concentration of sulfur trioxide in the reaction system is reduced.

[4] The process for producing 2-acrylamide-2-methylpropanesulfonic acid continuously, which comprises reacting acrylonitrile, fuming sulfuric acid and isobutylene, according to [3], wherein acrylonitrile, fuming sulfuric acid and isobutylene are fed into the reaction system continuously and reacted, the concentration of the 2-methyl-2-propenyl-1-sulfonic acid and/or 2-methylidene-1,3-propylenedisulfonic acid present in the reaction system is determined during the reaction and, when the concentration of 2-methyl-2-propenyl-1-sulfonic acid exceeds 12,000 mass ppm and/or the concentration of 2-methylidene-1,3-propylenedisulfonic acid exceeds 6,000 mass ppm, the concentration of sulfur trioxide in the fuming sulfuric acid fed into the reaction system is reduced to reduce the concentration of sulfur trioxide in the reaction system.

[5] The process for producing 2-acrylamide-2-methylpropanesulfonic acid continuously, which comprises reacting acrylonitrile, fuming sulfuric acid and isobutylene, according to claim 3, wherein acrylonitrile, fuming sulfuric acid and isobutylene are fed into the reaction system continuously and reacted, the concentration of the 2-methyl-2-propenyl-1-sulfonic acid and/or 2-methylidene-1,3-propylenedisulfonic acid present in the reaction system is determined during the reaction and, when the concentration of 2-methyl-2-propenyl-1-sulfonic acid exceeds 12,000 mass ppm and/or the concentration of 2-methylidene-1,3-propylenedisulfonic acid exceeds 6,000 mass ppm, the reaction time is increased to reduce the concentration of sulfur trioxide in the reaction system.

[6] A process for producing 2-acrylamide-2-methylpropanesulfonic acid, which comprises separating, by filtration, a crude 2-acrylamide-2-methylpropanesulfonic acid from the slurry obtained in the production process according to any of [3] to [5], to obtain a cake, and then washing the cake using a solvent selected from the group consisting of acrylonitrile, acetonitrile, acetone, methanol, ethanol, 2-propanol, butanol, ethyl acetate and acetic acid or a mixed solvent thereof.

[7] A process for producing 2-acrylamide-2-methylpropanesulfonic acid, which comprises separating, by filtration, a crude 2-acrylamide-2-methylpropanesulfonic acid from the slurry obtained in the production process according to any of [3] to [5], to obtain a cake, and then drying the cake at 60 to 130° C. for 10 to 300 minutes.

[8] A process for continuously producing 2-acrylamide-2-methylpropanesulfonic acid represented by the following formula (3),

[Formula 8]

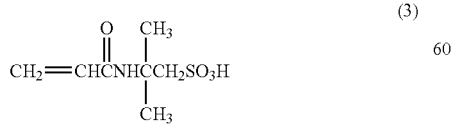

(3)

which comprises mixing acrylonitrile with fuming sulfuric acid in a first reaction vessel to obtain a mixture, feeding the mixture obtained in the first reaction vessel, into a second reaction vessel, reacting there the mixture with isobutylene, and taking out the resulting slurry from the second reaction vessel, wherein, when, in the taken-out slurry, the concentration of 2-methyl-2-propenyl-1-sulfonic acid represented by the following formula (1)

[Formula 9]

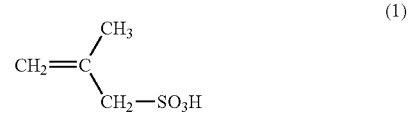

(1)

exceeds 12,000 mass ppm or the concentration of tert-butylacrylamide represented by the following formula (4)

[Formula 10]

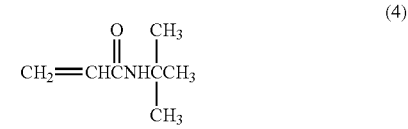

(4)

exceeds 10,000 ppm, the residence time of the mixture of acrylonitrile and fuming sulfuric acid in the first reaction vessel is increased to reduce the concentration of sulfur trioxide in the reaction system.

[9] A process for producing 2-acrylamide-2-methylpropanesulfonic acid, which comprises separating, by filtration, a crude 2-acrylamide-2-methylpropanesulfonic acid from the slurry obtained in the production process according to [8], to obtain a cake, and then washing the cake using a solvent selected from the group consisting of acrylonitrile, acetonitrile, acetone, methanol, ethanol, 2-propanol, butanol, ethyl acetate and acetic acid or a mixed solvent thereof.

[10] A process for producing 2-acrylamide-2-methylpropanesulfonic acid containing 2-methyl-2-propenyl-1-sulfonic acid at 30 mass ppm or lower, which comprises the following first to forth steps:

a first step of mixing fuming sulfuric acid with acrylonitrile of 7 to 30 moles relative to 1 mole of fuming sulfuric acid, for 90 minutes or longer, to produce a mixture of acrylonitrile and fuming sulfuric acid, a second step of contacting the mixture produced in the first step, with isobutylene at 40 to 70° C. for 90 to 180 minutes, to obtain an acrylonitrile slurry of 2-acrylamide-2-methylpropanesulfonic acid represented by the following formula (3)

[Formula 11]

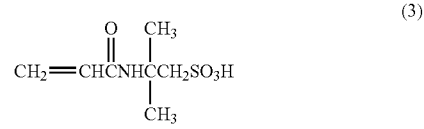

(3)

a third step of subjecting the slurry obtained in the second step, to solid-liquid separation to obtain a cake of crude 2-acrylamide-2-methylpropanesulfonic acid, and then washing the cake with acrylonitrile of mass of at least two times that of the cake, and a fourth step of drying the cake washed in the third step, at 80 to 130° C. for 30 to 300 minutes.

Advantageous Effects

The ATBS according to the first embodiment of the present invention is low in contents of IBSA and IBDSA. Accordingly, the polymer obtained by copolymerization of this ATBS has a large molecular weight.

In the process for producing ATBS, according to the first embodiment of the present invention, ATBS of high purity can be produced easily by measuring the amounts of by-products (IBSA and IBDSA) formed and controlling the concentration of sulfur trioxide. Therefore, the purification step, which is a later step, can be simplified.

In the process for producing ATBS, according to the second embodiment of the present invention, ATBS can be produced at a high yield. The ATBS produced in this process is low in contents of by-products such as tert-BAM, IBSA, IBDSA and the like. Therefore, a polymer obtained by copolymerization of this ATBS has a large molecular weight.

In the process for producing ATBS, according to the second embodiment of the present invention, ATBS of high purity can be produced easily. Therefore, the purification step, which is a later step, can be simplified.

The ATBS of the third embodiment of the present invention contains IBSA of 30 mass ppm or lower. Therefore, the copolymer obtained by copolymerization of this ATBS has a large molecular weight as compared with conventional copolymer. Since the copolymer obtained by copolymerization of the ATBS has a large molecular weight, the copolymer, when used, for example, as a coagulating agent or a thickening agent, can exhibit an intended effect even at a less addition amount, enabling cost reduction. Further, fluctuation in molecular weight by production lot is smaller.

In the process for producing ATBS, according to the third embodiment of the present invention, excessive sulfur trioxide is reduced as low as possible in the first step; a cake (a crude ATBS) is washed with acrylonitrile of at least two times the cake in the third step; then, the washed cake is heated and dried for decomposition and removal of IBSA; thereby, ATBS in which the content of IBSA is 30 mass ppm or lower, can be produced easily.

BRIEF DESCRIPTION OF THE DRAWINGS

FIG. 1 is a graph showing a relationship between the IBSA concentration in ATBS and the viscosity of the polymer obtained.

FIG. 2 is a graph showing a relationship between the IBSA concentration in ATBS and the viscosity of the polymer obtained.

FIG. 3 is a graph showing a relationship between the concentration of sulfur trioxide and the concentration of IBSA or IBDSA produced as a by-product, in the production of ATBS.

FIG. 4 is a graph showing a relationship between the residence time in reaction and the concentration of IBSA or IBDSA produced as a by-product.

FIG. 5 is a graph showing a relationship between the amount of solvent used for washing of cake and IBSA.

FIG. 6 is graph showing a relationship between the time and temperature used in the drying of cake and the IBSA concentration in cake.

FIG. 7 is a drawing showing the constitution of an example of the reaction equipment used in the present process for ATBS production.

FIG. 8 is a graph showing relationships between the excessive amount of sulfur trioxide and the concentrations of by-products.

FIG. 9 is a graph showing relationships between the residence time of fuming sulfuric acid and acrylonitrile and the concentrations of by-products, in the first reaction vessel.

FIG. 10 is a graph showing a relationship between the residence time of fuming sulfuric acid and acrylonitrile and the concentration of IBSA, in the first reaction vessel.

FIG. 11 is a graph showing a relationship between the amount of solvent used in washing of cake and IBSA.

FIG. 12 is a graph showing relationships between the drying time of washed cake and the concentration of IBSA.

2 is a first reaction vessel; 4 and 14 are each a jacket; 6 and 16 are each a temperature controller; 8 is acrylonitrile; 10 is fuming sulfuric acid; 12 is a second reaction vessel; 18 is isobutylene; 20 is a taking-out pipe; and 100 is a continuous production equipment.

BEST MODE FOR CARRYING OUT THE INVENTION

Invention of First Embodiment

2-Acrylamide-2-methylpropanesulfonic acid (ATBS)

The present invention is 2-acrylamide-2-methylpropanesulfonic acid (ATBS) represented by the following formula (3),

[Formula 12]

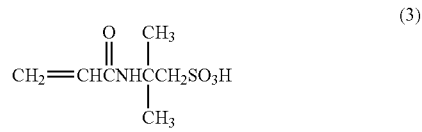

(3)

wherein the content of 2-methyl-2-propenyl-1-sulfonic acid (IBSA) represented by the following formula (1)

[Formula 13]

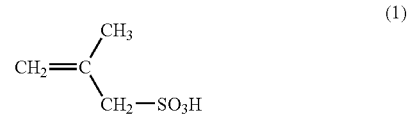

(1)

is 100 mass ppm or lower and the content of 2-methylidene-1,3-propylenedisulfonic acid (IBDSA) represented by the following formula (2)

[Formula 14]

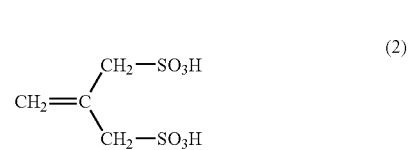

(2)

is 100 mass ppm or lower.

This ATBS contains IBSA and IBDSA each in an amount of 100 mass ppm or less and has a high purity. IBSA and IBDSA are each a by-product in ATBS production, as mentioned previously, and these compounds function as a chain transfer agent in radical polymerization reaction. Therefore, a polymer which is obtained by homopolymerization or copolymerization of ATBS or salt thereof, containing IBSA and IBDSA, has a small molecular weight. Further, the fluctuation in contents of these compounds causes the fluctuation in the molecular weight of the polymer obtained by homopolymerization or copolymerization of ATBS or salt thereof.

The present inventor confirmed, by the following experiment, that IBSA and IBDSA had a chain transfer action.

That is, IBSA was added to an aqueous solution of acrylamide and ATBS, in various amounts. Each of the resulting aqueous monomer solutions was subjected to polymerization to obtain various copolymers. Each copolymer was dissolved in water and the viscosity of each resulting aqueous solution was measured. The result is shown in FIG. 1.

The experiment was conducted according to the following procedure. First, 40 g of ATBS was dissolved in 60 g of water, and a 48 mass % aqueous NaOH solution was added thereto for adjustment of pH to 8. Water was added thereto for adjustment to a concentration of 35 mass %. 55.6 g of a 40 mass % aqueous acrylamide solution was added, followed by addition of 5.2 g of water, to adjust the total concentration of monomers to 35 mass %. Into the resulting aqueous monomers solution was blown nitrogen, and the temperature of the solution was adjusted to 30° C. Then, to the monomers solution were added 0.7 g of ammonium persulfate, 0.7 g of sodium sulfite, 0.6 g of an aqueous copper chloride solution containing 10 mass ppm of copper ion, and 0.7 g of an aqueous solution containing 10 mass % of V-50 (trade name, a product of Wako Pure Chemical Industries, Ltd.) as a diazo type radical polymerization initiator. A reaction was conducted for 2 hours, after which a copolymer formed was taken out.

1.15 g of the copolymer was dissolved in 393 g of water. Then, 23.4 g of sodium chloride was added to obtain a sample solution for viscosity measurement (copolymer concentration: 0.25 mass %). The viscosity measurement was conducted under the following conditions.

Viscometer: digital viscometer, a product of Brookfield
Rotor rpm: 60
Measurement temperature: 25° C.

It is clear from Table 1 that, as the addition amount of IBSA increases, the viscosity drops and the average molecular weight of the copolymer obtained decreases. It was confirmed from the data that IBSA acted as a chain transfer agent.

An experiment similar to that for IBSA was conducted for IBDSA. The result is shown in FIG. 2. It was confirmed from FIG. 2 that IBDSA acted as a chain transfer agent.

It was further confirmed from the results of FIGS. 1 and 2 that the conditions under which ATBS maintained high polymerizability to give a polymer of large molecular weight, were that each of IBSA content and IBDSA content in ATBS was 100 ppm or lower.

Process for Production of ATBS

The process for production of ATBS is described below.

2-Acrylamide-2-methylpropanesulfonic acid (ATBS) represented by the following formula (3) is produced by reacting acrylonitrile (5), sulfuric acid (6) and isobutylene (7) (each as a raw material), as shown in the following reaction formula (A). The reaction may be conducted by batch-wise or continuously.

$$CH_2=CHCN + H_2SO_4 + CH_2=C\underset{CH_3}{\overset{CH_3}{\diagup\!\!\!\diagdown}} \longrightarrow \quad (A)$$

(5)       (6)       (7)

-continued $$CH_2=CHC(=O)NHC(CH_3)_2CH_2SO_3H \quad (3)$$

In the reaction of acrylonitrile, sulfuric acid and isobutylene, firstly, acrylonitrile and sulfuric acid are mixed at a low temperature (about −15 to −10° C.) Then, isobutylene is blown into the resulting mixture with stirring the mixture. As a reaction begins, the temperature of the mixture increases owing to the heat of the reaction; therefore, it is preferred that the mixture is cooled to maintain the temperature at 40 to 50° C.

ATBS is formed by the equimolar reaction of the above-mentioned three raw material components. As the reaction proceeds, the reaction mixture becomes a slurry having a solid crystal of ATBS dispersed. The dispersing medium constituting the slurry is acrylonitrile added in a large excess relative to sulfuric acid and isobutylene.

The mixing proportions of the three raw material components are as follows. Sulfuric acid and isobutylene are mixed preferably in almost equimolar proportions. The proportion of acrylonitrile is 10 to 20 moles per 1 mole of sulfuric acid or isobutylene. By reacting a mixed fluid of such proportions, a slurry containing 15 to 25 mass % of a solid is obtained.

Incidentally, in the above reaction, the presence of water in the reaction system is not preferred because the water causes side reactions. Each of the above raw material components preferably contains no water. As to sulfuric acid, in particular, it is preferred to use a mixture of concentrated sulfuric acid and fuming sulfuric acid.

The slurry produced as above is then subjected to solid-liquid separation by centrifugation or the like and a crude crystal of ATBS is taken out. The crude crystal is then subjected to post-treatments such as washing, drying and the like, to obtain a high-purity product (ATBS).

In order to produce the high-purity ATBS, the below-described controls of reaction conditions are made in the present invention.

(First Control of Reaction Conditions)

In the first control, the amounts of by-products (IBSA and IBDSA) present in the reaction system are measured in the reaction for ATBS production, and the reaction conditions are controlled based on the amounts measured.

The control is conducted as follows. At first, the concentration of either of IBSA and IBDSA or the concentrations of both are measured. When the measured concentration of IBSA exceeds 12,000 ppm and/or when the concentration of IBDSA exceeds 6,000 ppm, the concentration of sulfur trioxide in the reaction system is controlled (reduced).

In order to reduce the concentration of sulfur trioxide, the amount of sulfur trioxide fed into the reaction system together with sulfuric acid may be decreased or the feeding of sulfur trioxide may be stopped.

The amounts of IBSA and IBDSA present in the reaction system may be measured by any method. The measurement by high performance liquid chromatography (hereinafter abbreviated as HPLC) is preferred for easy measurement and accurate measurement.

FIG. 3 is a graph obtained by actually measuring, in the reaction for ATBS production, the relationship between the excessive amount of sulfur trioxide and the concentration of IBSA or IBDSA, present in the reaction system. It is appreciated from this graph that an increase in sulfur trioxide in the reaction system causes an increase in IBSA and IBDSA. Incidentally, the excessive amount of sulfur trioxide indicates the amount (mass %) of sulfur trioxide present in excess relative to 100% sulfuric acid.

By controlling the reaction conditions as above, there is obtained a slurry of ATBS containing ordinarily 12,000 mass ppm or less of IBSA and 6,000 mass ppm or less of IBDSA.

(Second Control of Reaction Conditions)

In the second control, the amounts of by-products (IBSA and IBDSA) present in the reaction system are measured and, when the concentration of IBSA exceeds 12,000 mass ppm and/or when the concentration of IBDSA exceeds 6,000 mass ppm, the reaction time is controlled (extended).

FIG. 4 shows a graph obtained by actually measuring the relationship between the IBSA or IBDSA present in the reaction system and the time of reaction. It is confirmed from this graph that, when the reaction time is extended, the concentration of IBSA decreases while the concentration of IBDSA increases for a while and then decreases. Accordingly, it is appreciated that, when the concentrations of IBSA and IBDSA in the reaction system are high, control should be made so as to extend the reaction time. In order to extend the reaction time, the residence time of the reaction mixture in reactor may be extended, for example, when a continuous production equipment is used.

By controlling the reaction conditions as above, there is obtained a slurry of ATBS containing ordinarily 12,000 mass ppm or less of IBSA and 6,000 mass ppm or less of IBDSA.

Next, crude ATBS is isolated from the above-obtained slurry. The isolation is conducted, for example, by subjecting the slurry to solid-liquid separation to obtain crude ATBS. A cake containing crude ATBS is obtained by the solid-liquid separation and then the cake is dried. Since the crude ATBS obtained contains a large amount of impurities such as IBSA, IBDSA and the like, the crude ATBS cannot be used per se for production of a polymer of high molecular weight. Therefore, the cake is purified in the purification step.

In an example of the purification step, the cake obtained by subjecting the slurry to solid-liquid separation is washed using acrylonitrile. In-depth investigation was made on the changes of concentrations of the IBSA and IBDSA contained in the cake, in the washing of the cake. The result is shown in FIG. 5. The contents of IBSA and IBDSA in crude ATBS decrease in proportion to the increase in the amount of acrylonitrile used as a washing solvent. The same purification is possible also with a solvent other than acrylonitrile.

The cake obtained by subjecting the slurry to solid-liquid separation is washed by a solvent such as acrylonitrile or the like and the washed cake is dried to remove the solvent, whereby an ATBS product is obtained. The use amount (mass) of the washing solvent is preferably 0.5 to 10 times, preferably 1 to 3 times the mass of the solid content of the cake to be washed. Preferred as the washing solvent are acrylonitrile, acetonitrile, acetone, methanol, ethanol, 2-propanol, butanol, ethyl acetate, acetic acid, etc., and a mixed solvent thereof. Particularly preferred is acrylonitrile.

The cake separated from the slurry is washed by the washing solvent, whereby the cake is purified. The concentrations of IBSA and IBDSA in the cake are each reduced to 100 mass ppm or lower.

The drying step has heretofore been conducted in order to remove the solvent contained in the cake.

The present inventor investigated on the changes, in the drying step, of the concentrations of impurities such as IBSA, IBDSA and the like. As a result, it was found that, when the drying conditions are controlled in the drying step, IBSA and IBDSA could be decreased and the quality of the product obtained could be enhanced.

FIG. 6 is graph showing a relationship between the temperature and time used in the drying of washed cake and the IBSA concentration in product cake. It is considered that these compounds, when heated, cause thermal decomposition and decrease in amounts.

The graph indicates that, when the washed cake is dried at 60 to 130° C. for 10 to 300 minutes, the IBSA and IBDSA concentrations in washed cake can be decreased.

For example, when sulfur trioxide becomes excessive in the reaction and the content of IBSA increases, or when the washing of cake is insufficient in the solid-liquid separation step and the IBSA content cannot be lowered, or when the cake washing is omitted in the above step, the IBSA and IBDSA concentrations in product can be decreased by taking a measure such as (1) elevation of drying temperature or (2) extension of drying time, based on the data of FIG. 6.

Invention of Second Embodiment

Firstly, the reaction between acrylonitrile, sulfuric acid and isobutylene was investigated in depth and the facts described in the following Table 1 were confirmed.

TABLE 1

| Compounds formed in presence of water | Compounds formed in presence of SO$_3$ |
| --- | --- |
| Acrylamide | IBSA |
| Tert-BAM | IBDSA |

The basic concept in setting of reaction conditions in the second embodiment is to remove water from the reaction system and to minimize the concentration of sulfur trioxide.

Then, a test for production of ATBS was conducted using a continuous production equipment shown in FIG. 7. In FIG. 7, 100 is a continuous production equipment for ATBS. 2 is a first reaction vessel provided with a stirring device not shown and is covered outside with a jacket 4. Into the jacket 4 is fed a temperature-controlling fluid from a first temperature controller 6, whereby the temperature inside the first reaction vessel 2 is controlled. Into the first reaction vessel 2 are continuously fed acrylonitrile 8 and fuming sulfuric acid 10, and they are stirred by the stirring device not shown. This stirring produces a mixed fluid thereof continuously. In this case, the water in acrylonitrile reacts with the sulfur trioxide in fuming sulfuric acid, to become sulfuric acid, whereby the water is removed.

The mixed fluid produced in the first reaction vessel 2 is sent to a second reaction vessel 12. A jacket 14 is formed on the outer surface of the second reaction vessel 12. The temperature inside the second reaction vessel 12 is controlled by a temperature-controlling fluid sent to the jacket 14 from a second temperature-controller 16.

Isobutylene 18 is fed into the mixed fluid sent into the second reaction vessel. Inside the second reaction vessel 12, the mixed fluid sent from the first reaction vessel 2 is reacted with isobutylene to form ATBS. The ATBS formed is suspended in the acrylonitrile fed in excess and acting as a solvent. As a result, a slurry of ATBS is formed. This slurry is taken outside continuously through a taking-out pipe 20 fitted to the second reaction vessel 12. The slurry taken out is sent to a purification step not shown and purified there.

ATBS was produced using the above continuous production equipment. First, acrylonitrile and fuming sulfuric acid were fed continuously into the first reaction vessel 2 and mixed at −10 to −15° C. to produce a mixed fluid. The residence time of the mixed fluid in the first reaction vessel was 20 minutes. The concentration of sulfur trioxide was controlled by controlling the mixing ratio of fuming sulfuric acid and concentrated sulfuric acid.

Then, the mixed fluid was sent into the second reaction vessel 12, where the mixed fluid was reacted with isobutylene. The reaction temperature was 45° C. and the residence time in the second reaction vessel 12 was 60 minutes.

The slurry of acrylonitrile containing formed ATBS was taken outside through the taking-out pipe 20. The taken-out slurry was subjected to solid-liquid separation in a purification step. The solid and the liquid both obtained were each analyzed to measure the concentrations of by-products contained therein.

In the first reaction vessel 2, acrylonitrile and fuming sulfuric acid are mixed and the water in acrylonitrile is removed. Relationships between the amounts of sulfur trioxide remaining after removal of water and the amounts of tert-BAM, IBSA and IBDSA in the slurry taken out from the second reaction vessel 12 are shown in FIG. 8.

IBSA and IBDSA have a chain transfer action, as described previously. Therefore, when ATBS containing large amounts of these compounds is copolymerized with other monomer, the polymer obtained has a small molecular weight.

It is assumed from FIG. 8 that the concentrations of formed IBSA and IBDSA, in which their chain transfer actions can be neglected practically, are each 10,000 mass ppm. In this case, the excessive amount of sulfur trioxide corresponding to the above concentrations is 0.3 mass %. Fixing the excessive amount of sulfur trioxide at 0.3 mass %, the residence time of the mixed fluid in the first reaction vessel 2 was varied. Relationships obtained between the residence time and the concentrations of by-products are shown in FIG. 9.

As is clear from FIG. 9, a longer mixing time between acrylonitrile and fuming sulfuric acid (a longer residence time in the first reaction vessel) results in lower concentrations of by-products (tert-BAM and IBSA). Thus, it is appreciated that, when the water in acrylonitrile is removed by sulfur trioxide of low concentration, a somewhat long mixing time is needed. A longer mixing time results in a smaller water amount in the mixing fluid. Further, the excessive amount of sulfur trioxide decreases. As a result, the above-mentioned basic concept can be realized. The production process of the second embodiment of the present invention was completed based on the above investigation results.

Production Process of ATBS

Description is made below on the continuous production process of ATBS, of the second embodiment, in which the above investigation result has been reflected.

In producing ATBS by reacting acrylonitrile, sulfuric acid and isobutylene, first, acrylonitrile and sulfuric acid are mixed in the first reaction vessel at a low temperature (about −15 to −10° C.) In this case, a mixing time need be long in order to remove the water in acrylonitrile completely. The control of the mixing time is achieved by controlling the residence time of the mixed fluid of acrylonitrile and sulfuric acid in the first reaction vessel. The residence time is ordinarily 30 minutes or longer, preferably 40 to 360 minutes. The mixture is transferred into the second reaction vessel and isobutylene is blown into the mixture with stirring. This operation is conducted continuously. With the start of a reaction, the temperature of the mixture increases owing to the heat of the reaction; therefore, the reaction mixture is cooled. The temperature of the reaction mixture is maintained preferably at 40 to 50° C.

ATBS is formed by an equimolar addition reaction of the above-mentioned three raw material components. With the progress of the reaction, the reaction mixture becomes a slurry in which ATBS solid crystal is dispersed. The dispersing medium in the slurry is acrylonitrile used in a large excess relative to sulfuric acid and isobutylene.

The mixing proportions of the three raw material components are as described below. The mixing proportions of sulfuric acid and isobutylene are preferably about equimolar. The mixing proportion of acrylonitrile relative to sulfuric acid or isobutylene is 10 to 20 moles per 1 mole of sulfuric acid or isobutylene. By reacting the mixed fluid of such mixing proportions, there can be obtained, as a reaction mixture, a slurry containing 15 to 25 mass % of a solid.

As described previously, the presence of water in the reaction system is not preferred because the water causes side reactions. Accordingly, any of the above three raw material components is preferably free from water. As to sulfuric acid, in particular, a mixture of concentrated sulfuric acid and fuming sulfuric acid is used preferably.

The slurry produced as above is then subjected to solid-liquid separation by an operation such as centrifugation or the like and a crystal of crude ATBS is taken out. This crude ATBS is subjected to post-treatments such as washing, drying and the like, to obtain a product (ATBS).

In the invention of the second embodiment, there is first measured, in the reaction of ATBS production, the concentration of the by-product IBSA or tert-BAM in the slurry taken outside from the second reaction vessel through the taking-out pipe 20. Then, when the measured concentration of IBSA exceeds 12,000 mass ppm or the measured concentration of tert-BAM exceeds 10,000 mass ppm, the residence time of the mixture of acrylonitrile and fuming sulfuric acid in the first reaction vessel 2 is increased. By conducting this operation, high-purity ATBS can be produced.

The measurement of the concentration of IBSA or tert-BAM may be conducted by any method. The measurement by high performance liquid chromatography (abbreviated as HPLC) is preferred from the standpoints of the easiness and accuracy of measurement.

By controlling the reaction conditions as above, there can be obtained a slurry in which the concentration of IBSA in ATBS is ordinarily 12,000 mass ppm or lower and the concentration of IBDSA in ATBS is ordinarily 6,000 mass ppm or lower.

Then, crude ATBS is isolated from the ATBS-containing slurry obtained by the reaction conducted under the above controls. The isolation may be made by subjecting the slurry to solid-liquid separation to separate a cake containing crude ATBS and drying the cake. The resulting crude ATBS contains large amounts of impurities such as tert-BAM, IBSA, IBDSA and the like and, therefore, cannot be used per se for production of a high-molecular weight polymer. Accordingly, the cake is purified in a purification step.

In an example of the purification step, the cake obtained by solid-liquid separation of slurry is washed with acrylonitrile. Use of a larger amount of acrylonitrile (as a washing solvent) results in removal of IBSA and IBDSA from ATBS at higher ratios. The same purification is possible with a solvent other than acrylonitrile.

The cake obtained by the solid-liquid separation of slurry is washed with a solvent such as acrylonitrile or the like and the washed cake is dried to remove the solvent, whereby a product (ATBS) can be obtained. The use amount (mass) of the washing solvent is preferably 0.5 to 10 times the mass of the solid content of cake, more preferably 1 to 3 times. As the washing solvent, there are preferred acrylonitrile, acetonitrile, acetone, methanol, ethanol, 2-propanol, butanol, ethyl acetate, acetic acid, etc., and a mixed solvent thereof. Acrylonitrile is preferred particularly.

The cake separated from the slurry is washed with the washing solvent, whereby the cake is purified and the IBSA and IBDSA concentrations therein becomes ordinarily 100 mass ppm or lower.

By the above production process, formation of by-products are suppressed and the yield of ATBS is ordinarily higher than 90%.

Invention of Third Embodiment

2-Acrylamide-2-methylpropanesulfonic acid (ATBS)

The ATBS of the present invention contains 2-methyl-2-propenyl-1-sulfonic acid (IBSA) in an amount of 30 mass ppm or less, preferably 20 mass ppm or less. There is no particular restriction as to the lower limit of IBSA content, and the IBSA content is preferably as low as possible. Making the content lower than 1 mass ppm industrially involves considerable difficulty. When the ATBS content exceeds 30 mass ppm, the copolymer obtained by copolymerization of ATBS may have no sufficiently large molecular weight. Such ATBS may be unusable in production of a high-molecular polymer used, for example, as a thickening agent of cosmetic, a chemical for crude oil drilling, or a chemical for higher-order recovery of crude oil. The molecular weight sufficiently satisfactory in the above applications is ordinarily 1,000,000 or larger in terms of average molecular weight.

The content of IBSA is measured by HPLC.

Incidentally, the chain transfer action of IBSA was already mentioned in the invention of first embodiment.

There has been no commercial ATBS containing IBSA in an amount of 40 mass ppm or less.

Production Process of ATBS

Description is made below on the present production process of IBSA containing IBSA in an amount of 30 mass ppm or less.

The present production process comprises the following first to fourth steps.

(First Step)

In the first step, acrylonitrile and fuming sulfuric acid are mixed to produce a mixed fluid thereof. The use amount of acrylonitrile is preferably 7 to 30 moles, more preferably 10 to 20 moles per 1 mole of isobutylene described later. The use amount of fuming sulfuric acid is approximately equimolar to the isobutylene described later. By conducting a reaction using this mixed fluid, there is obtained, as described later, a slurry in which IBSA formed is dispersed in acrylonitrile.

By mixing fuming sulfuric acid with acrylonitrile, the water in acrylonitrile is reacted with the sulfur trioxide in fuming sulfuric acid and removed. The use amount of fuming sulfuric acid is such that the excessive amount of sulfur trioxide remaining after water removal becomes preferably 0.6 mass % or less, more preferably 0.3 mass % or less, particularly preferably 0 to 0.2 mass %.

As described previously, FIG. 3 shows a relationship between the excessive amount of sulfur trioxide and the concentration of by-produced IBSA, when acrylonitrile, fuming sulfuric acid and isobutylene are reacted to produce ATBS. As is clear from FIG. 3, feeding of sulfur trioxide in excess causes an increase in IBSA concentration.

The mixing time between acrylonitrile and fuming sulfuric acid (the residence time in the first reaction vessel in the case of continuous production) is 90 minutes or longer, more preferably 90 to 360 minutes, particularly preferably 120 to 180 minutes. When the mixing time is shorter than 90 minutes, the water in acrylonitrile is not removed sufficiently; unreacted water and sulfur trioxide remain in the mixed fluid; the IBSA content in final product exceeds 30 mass ppm.

As described previously, FIG. 10 shows a relationship between the mixing time of acrylonitrile and sulfur trioxide and the content of by-produced IBSA when acrylonitrile, fuming sulfuric acid and isobutylene are reacted to produce ATBS. It is clear from FIG. 10 that the mixing time is required to be at least 90 minutes, preferably at least 120 minutes in order to sufficiently remove the water in acrylonitrile.

The temperature of mixing between acrylonitrile and sulfur trioxide is preferably −15 to 0° C., more preferably −10 to −5° C. When the mixing temperature exceeds 0° C., there tend to occur the coloring of product and the formation and mixing into product, of acrylonitrile polymer.

A stirrer is preferably used in the mixing.

(Second Step)

In the second step, the above-produced mixed fluid is contacted with isobutylene. The contact is conducted, for example, by blowing isobutylene into the mixed fluid. The reaction temperature is 40 to 70° C., preferably 50 to 60° C., and the reaction time is 90 to 180 minutes, preferably 100 to 160 minutes. The contact of the mixed fluid with isobutylene causes progress of a reaction and formation of ATBS. As the reaction proceeds, the reaction mixture becomes a slurry in which solid particles of formed ATBS are dispersed in acrylonitrile. Finally, there is formed a slurry containing a solid content by 15 to 25 mass %. This slurry contains IBSA (by-product) of ordinarily about 6,000 to 12,000 mass ppm.

(Third Step)

In the third step, the slurry is subjected to solid-liquid separation to obtain a cake of crude ATBS. The solid-liquid separation can be conducted by any of filtration, centrifugation, etc. Then, the separated cake is washed with acrylonitrile (AN). The amount (mass) of acrylonitrile used in the washing is 2 times, preferably 3 to 10 times the mass of the cake.

As described previously, FIG. 11 shows a relationship between the use amount of acrylonitrile and the IBSA concentration in the cake after washing when the cake obtained in the third step is washed with acrylonitrile. It is clear from FIG. 11 that use of acrylonitrile in amount (mass) of at least two times the mass of the cake, in the washing of the cake can reduce the IBSA concentration in the cake after washing, to 100 mass ppm or lower.

(Fourth Step)

In the fourth step, the washed cake obtained in the third step is heated and dried at 80 to 130° C., preferably 90 to 120° C. The drying time is 30 to 300 minutes, preferably 50 to 200 minutes.

As described previously, the heating and drying incurs decomposition of IBSA. As a result, ATBS of 30 mass ppm or lower in IBSA content is produced.

FIG. 12 shows a relationship between the drying time and the IBSA concentration in cake when a cake containing IBSA in an amount of 4,000 mass ppm is heated and dried. It indicates that a longer drying time greatly reduces the IBSA concentration in cake.

In the fourth step, the washed cake after the third step containing IBSA in a concentration of about 100 mass ppm is heated and dried under the above-mentioned conditions. By this heating operation, there can be obtained an ATBS cake of the present invention containing IBSA in a concentration of 30 mass ppm or lower.

In the above ATBS production, ATBS can be produced batch-wise or continuously.

EXAMPLES

The present invention is described specifically below by way of Examples. The concentration shown in each Example is a concentration quantitatively determined by HPLC.

HPLC condition: high performance liquid chromatograph produced by Waters
Column: ODS-3 produced by GL Science
Elutant: 0.03% aqueous trifluoroacetic acid solution/acetonitrile
Flow rate of elutant: 0.8 ml/min
Detection wavelength: 200 nm Invention of First Embodiment Example 1

Two glass reactors each provided with a stirrer, an inlet pipe and an outlet pipe were connected to each other. Acrylonitrile and fuming sulfuric acid were fed into the first reactor under the following conditions. They were mixed and the mixed fluid thereof was fed into the second reactor. In the second reactor, isobutylene gas was blown into the mixed fluid to synthesize ATBS. The reaction (synthesis) was conducted continuously.

Acrylonitrile and isobutylene were fed into respective reactors at proportions of 11 mole and 0.9 mole, respectively, both relative to 1 mole of fuming sulfuric acid. The feeding rate of fuming sulfuric acid was 1.6 mole/hour and the reaction was continuously conducted for 12 hours. During the reaction, a sample of the reaction mixture was taken and measured for IBSA and IBDSA concentrations by HPLC and the feeding amount of fuming sulfuric acid was controlled as shown in Table 2.

Incidentally, the concentration of sulfur trioxide in fuming sulfuric acid is 0.6%. By considering the water introduced from the raw materials such as acrylonitrile, concentrated sulfuric acid was mixed into commercial 20% fuming sulfuric acid to control the concentration of sulfur trioxide. The first reactor was kept at −5 to −15° C. and the residence time therein was 10 minutes. The second reactor was kept at 30 to 50° C. and the residence time therein was 90 minutes.

The ATBS slurry obtained in the above production was suction-filtered using a glass filter to obtain a cake on the glass filter. Acrylonitrile of an amount (mass) shown in Table 2, relative to the mass of the cake was poured onto the cake. Suction filtering was conducted again to wash the cake with acrylonitrile.

The washed cake was transferred onto a tray and dried for 90 minutes at a temperature of 80° C.

The ATBS powder obtained was analyzed by HPLC to measure the concentrations of IBSA and IBDSA.

Then, using the ATBS obtained above, a copolymer of ATBS and acrylamide was produced.

Production of the copolymer was conducted according to the following procedure. First, 40 g of the ATBS was dissolved in 60 g of water. Thereto was added a 48 mass % aqueous NaOH solution for adjustment of pH to 8. Thereto was added water to control the concentration of ATBS at 35 mass %. 55.6 g of a 40 mass % aqueous acrylamide solution was added, followed by addition of 5.2 g of water, to control the concentration of monomers at 35 mass %. Nitrogen was blown into the resulting aqueous monomers solution (during the period, the solution temperature was controlled at 30° C.) Then, there were added 0.7 g of ammonium persulfate, 0.7 g of sodium sulfite, 0.6 g of an aqueous copper chloride solution containing 10 mass ppm of copper ion, and 0.7 g of an aqueous solution containing 10 mass % of V-50 (a product of Wako Pure Chemical Industries, Ltd.) as a diazo type radical polymerization initiator. A reaction was complete in 2 hours and then a copolymer was taken out.

1.15 g of this copolymer was dissolved in 393 g of water. 23.4 g of sodium chloride was added to obtain a sample solution for viscosity measurement (copolymer concentration: 0.25 mass %).

The sample solution for viscosity measurement was measured for viscosity. The viscosity measurement was conducted under the following conditions.

Viscometer: Digital viscometer (a product of Brookfield)
Rotor revolution: 60 rpm
Measurement temperature: 25° C.
The result is shown in Table 2.

Example 2

In Example 1, the amount of acrylonitrile used for cake washing was halved. Since the remaining of IBSA could be predicted from the data of FIG. 5, drying was conducted at 110° C. (higher than ordinary drying temperature) for 90 minutes, in order to reduce IBSA. The ATBS powder obtained was analyzed by HPLC. A copolymer of ATBS and acrylamide was produced in the same manner as in Example 1. The copolymer was measured for viscosity in the same manner as in Example 1. The result is shown in Table 2.

Example 3

An operation was conducted in the same manner as in Example 1 except that the cake was dried at 110° C. The ATBS powder obtained was analyzed by HPLC. A copolymer of ATBS and acrylamide was produced in the same manner as in Example 1. The copolymer was measured for viscosity in the same manner as in Example 1. The result is shown in Table 2.

Example 4

An operation was conducted in the same manner as in Example 3 except that the cake was washed with acetic acid. The ATBS powder obtained was analyzed by HPLC. A copolymer of ATBS and acrylamide was produced in the same manner as in Example 1. The copolymer was measured for viscosity in the same manner as in Example 1. The result is shown in Table 2.

Example 5

ATBS was produced by, in Example 1, changing the concentration of sulfur trioxide to 2% and the residence time in reaction to 120 minutes. Further, the washed cake was dried at 110° C. for 180 minutes. The ATBS powder obtained was analyzed by HPLC. A copolymer of ATBS and acrylamide was produced in the same manner as in Example 1. The copolymer was measured for viscosity in the same manner as in Example 1. The result is shown in Table 2.

TABLE 2

| | | Example 1 | Example 2 | Example 3 | Example 4 | Example 5 | Comp. Example 1 |
|---|---|---|---|---|---|---|---|
| Reaction conditions | Excessive amount of $SO_3$ (mass %) | 0.6 | 0.6 | 0.6 | 0.6 | 2 | 0.6 |
| | Residence time (min) | 90 | 90 | 90 | 90 | 120 | 90 |
| Washing of cake | Washing solvent | AN | AN | AN | Acetic acid | AN | AN |
| | Ratio of solvent to cake solid (based on mass) | 2 times | 1 time | 2 times | 2 times | 2 times | 2 times |
| Drying of cake | Drying temperature (° C.) | 80 | 110 | 110 | 110 | 110 | 80 |
| | Drying time (min) | 90 | 90 | 60 | 30 | 180 | 90 |
| Concentrations of impurities and polymerizability | IBSA (mass ppm) | 100 | 90 | 60 | 60 | 80 | 150 |
| | IBDSA (mass ppm) | 80 | 100 | 60 | 60 | 100 | 80 |
| | UL viscosity (mPa · s) | 3.0 | 3.0 | 3.3 | 3.3 | 3.1 | 2.6 |

AN: acrylonitrile

Comparative Example 1

ATBS was synthesized continuously in the same manner as in Example 1 except that the concentrations of IBSA and IBDSA were not analyzed by HPLC during the reaction and the initial proportions of feeding were maintained. After the completion of the reaction, a sample of the reaction mixture was taken and measured for the concentrations of IBSA and IBDSA by HPLC, which indicated an IBSA concentration of 15,000 mass ppm and an IBDSA concentration of 2,000 mass ppm. The ATBS slurry obtained was suction-filtered using a glass filter to obtain a cake on the glass filter. The cake was washed by pouring, onto the cake, acrylonitrile of an amount (mass) of two times the mass of solid content of the cake to again conduct suction filtration. The washed cake was transferred onto a tray and dried at 80° C. for 90 minutes. The ATBS powder obtained was analyzed by LC to measure the concentrations of IBSA and IBDSA, which indicated an IBSA concentration of 150 mass ppm and an IBDSA concentration of 80 mass ppm.

The ATBS was examined for polymerizability, which indicated a UL viscosity of 2.6 mPa·s.

The excessiveness of sulfur trioxide was set at the same level as in Example 1. However, during the production of ATBS, the actual excessiveness of sulfur trioxide varies depending upon the slight variations of the concentration of fuming sulfuric acid, the concentration of concentrated sulfuric acid and the water contained in the raw materials used. In Comparative Example 1, no measurement of impurities in reaction mixture, for correction of reaction conditions was made during the reaction. In Comparative Example 1, the reaction continued with maintaining the feeding amount of sulfur trioxide at the initially set level; therefore, the concentrations of IBSA and IBDSA fluctuated and the quality of the ATBS obtained was low. When ATBS is produced under such production conditions, the variation of impurity concentrations among production lots is large.

Reference Test Examples 1 and 2, and Comparative Reference Test Example 1

40 g of ATBS was dissolved in 40 g of pure water. A 16.25 mass % aqueous sodium hydroxide solution was added for pH adjustment to 8 to 8.5. In this case, the solution temperature was measured and the solution was cooled as necessary so that the temperature did not exceed 25° C. After the pH adjustment, pure water was added to prepare 146 g of an aqueous solution containing 30.3 wt. % of neutralized ATBS. In a separate vessel were placed 370.2 g of a 40 mass % aqueous acrylamide solution, 66.5 g of the above-prepared aqueous solution of neutralized ATBS and 363.4 g of pure water, and they were mixed. This mixed monomers solution was measured for pH, which was 6.8. The mixed monomers solution was transferred into a polymerization vessel and nitrogen of 2 liters/min was blown thereinto. After 1 hour, the solution temperature was controlled at 20° C. while continuing the blowing of nitrogen.

To the monomers solution were added 0.39 ml of a 100 mass ppm aqueous copper solution, 3.02 ml of a 10 mass % aqueous V-50 solution and 2.02 ml of 1 mass % ammonium persulfate. After 15 minutes, the nitrogen blowing into monomers solution was terminated, and the blowing of nitrogen (40 ml/min) into the gaseous phase of polymerization vessel was started. The solution temperature increased gradually owing to the heat of polymerization, reached 70° C. after 2 hours, and then decreased gradually. After 8 hours, the gel of formed polymer was taken out and cooled. The gel was cut using a meat chopper. The cut gel was dried at 80° C. for 3 hours. The dried gel was ground using a grinder. The polymer powder obtained was dissolved in water and measured for properties, according to the following methods.

(Salt Viscosity)

2.26 g of the polymer powder obtained in the above operation was placed in a 500-ml vessel and 400 ml of pure water was added thereto. The powder was dissolved using a jar tester (200 rpm, 5 hours of stirring). Then, 16 g of sodium chloride was added. Stirring was made for 30 minutes to obtain a solution for measurement of salt viscosity.

The measurement of viscosity was conducted using a B type viscometer at a solution temperature of 25° C. The result of the measurement is shown in Table 3.

(Water-Insoluble)

0.5 g of the polymer powder obtained in the above operation was placed in a 500-ml vessel and 500 ml of pure water was added thereto. The powder was dissolved using a jar tester (200 rpm, 5 hours of stirring) to obtain a solution for measurement of insoluble.

The measurement of insoluble was conducted by poring the above solution onto an 80-mesh sieve and, after 10 minutes, transferring the gel remaining on the sieve, into a graduated cylinder and measuring the volume thereof. The result of the measurement is shown in Table 3.

(Stringiness)

1.5 g of the polymer powder obtained in the above operation was placed in a 500-ml vessel and 500 ml of pure water was added thereto. The powder was dissolved using a jar tester (200 rpm, 5 hours of stirring) to obtain a solution for measurement of stringiness.

Stringiness was measured at a solution temperature of 25° C. at a lowering speed of 5 mm/sec. The result of the measurement is shown in Table 3.

The method for measurement of stringiness is described below. First, a sample solution-containing vessel is placed on a pedestal whose lowering speed has been controlled at 5 mm/sec. Meanwhile, a glass bead (diameter: 10 mm) is suspended from above the sample solution vessel. The glass bead is immersed in the sample solution so that the lower end of the glass bead is positioned 27 mm below the sample solution surface. In this state, the pedestal is lowered at a speed of 5 mm/sec. There is measured a time taken from the moment of separation of the lower end of glass bead from sample solution surface, to the moment of cutting of string from glass bead. A value obtained by multiplying the time by the lowering speed (5 mm/sec) of the pedestal is taken as stringiness (mm).

TABLE 3

| | Reference Test Example 1 | Reference Test Example 2 | Comparative Reference Test Example 3 |
|---|---|---|---|
| ATBS used in Test | Product of Example 1 | Product of Example 3 | Product of Comparative Example 1 |
| Salt viscosity (mPa·s) | 148 | 155 | 125 |
| Insoluble (ml) | 9 | 0 | 0 |
| Stringiness (mm) | 57 | 62 | 37 |

As is clear from the values of salt viscosity and stringiness, control of reaction so as to give IBSA and IBDSA concentrations each of 100 mass ppm or lower allows for production of a high-molecular weight polymer.

Invention of Second Embodiment

The present invention of the second embodiment is described specifically below by way of Examples. The concentration shown in each Example is a concentration quantitatively determined by the following HPLC.

HPLC condition: high performance liquid chromatograph produced by Waters
Column: X-bridge Shield RP 18 [column size: 4.6 mm (inner diameter)×150 mm (length)], a product of Waters
Elutant: 0.03 mass % aqueous trifluoroacetic acid solution/acetonitrile (90/10 by volume)
Flow rate of elutant: 0.8 ml/min
Detection wavelength: 200 nm Comparative Example 2

Two glass reaction vessels each provided with a stirrer, an inlet pipe and an outlet pipe were connected to each other to constitute a first reaction vessel and a second reaction vessel. Acrylonitrile and fuming sulfuric acid were fed into the first reaction vessel under the following conditions and were mixed. Then, the mixed fluid was fed into the second reaction vessel. In the second reaction vessel, isobutylene gas was blown into the mixed fluid to synthesize ATBS. The reaction (synthesis) was conducted continuously.

Acrylonitrile and isobutylene were fed into respective reactors at proportions of 11 mole and 0.9 mole, respectively, both relative to 1 mole of fuming sulfuric acid. The feeding amount of fuming sulfuric acid was 1.4 mole/hour and the reaction was continuously conducted for 8 hours.

Incidentally, the concentration of sulfur trioxide in fuming sulfuric acid was 0.3 mass %. By considering the water introduced from the raw materials such as acrylonitrile, concentrated sulfuric acid was mixed into commercial 20 mass % fuming sulfuric acid to control the concentration of sulfur trioxide. The first reaction vessel was kept at −15° C. and the residence time therein was 10 minutes. The second reaction vessel was kept at 45° C. and the residence time therein was 60 minutes.

The slurry was taken out from the taking-out pipe fitted to the second reaction vessel and analyzed by HPLC. The amount of tert-BAM was 11,000 mass ppm.

The ATBS slurry obtained in the above production was suction-filtered using a glass filter to obtain a cake on the glass filter. Acrylonitrile of an amount (mass) of two times the solid content mass of cake was poured onto the cake. Suction filtering was conducted again to wash the cake.

The washed cake was transferred onto a tray and dried for 90 minutes at a temperature of 80° C.

The ATBS powder obtained was measured for mass and its yield based on isobutylene was calculated. Purity analysis was conducted by HPLC. The result is shown in Table 4.

Comparative Example 3

An operation was conducted in the same manner as in Comparative Example 2 except that the conditions shown in Table 4 were used. The result is shown in Table 4.

Examples 6 to 9

An operation was conducted in the same manner as in Comparative Example 2 except that the conditions shown in Table 4 were used. In Comparative Examples 2 and 3, since the residence time in the first reaction vessel was short, the contents of tert-BAM and IBSA were high. In Examples 6 to 9, since the residence time in the first reaction vessel was long, the contents of tert-BAM and IBSA in the slurry were decreased. The results are shown in Table 4.

TABLE 4

| | | Example 6 | Example 7 | Example 8 | Example 9 | Comp. Example 2 | Comp. Example 3 |
|---|---|---|---|---|---|---|---|
| First reaction vessel | Excessive amount of SO₃ | 0.3 | 0.3 | 0.6 | 0.3 | 0.3 | 0.6 |
| | Residence time (min) | 40 | 80 | 40 | 30 | 10 | 20 |
| | Temperature (° C.) | −15 | −15 | −15 | −15 | −15 | −15 |

TABLE 4-continued

|  |  | Example 6 | Example 7 | Example 8 | Example 9 | Comp. Example 2 | Comp. Example 3 |
|---|---|---|---|---|---|---|---|
| Second reaction vessel | Temperature (° C.) | 45 | 45 | 45 | 55 | 45 | 45 |
|  | Residence time (min) | 120 | 120 | 120 | 60 | 60 | 60 |
| Concentrations in slurry (mass ppm) | Tert-BAM | 8000 | 4000 | 4000 | 8000 | 11000 X | 8000 |
|  | IBSA | 6000 | 4000 | 12000 | 12000 | 12000 | 16000 X |
| ATBS | Yield (%) | 94 | 94 | 95 | 92 | 88 | 90 |
|  | Purity (%) | 99.4 | 99.5 | 99.4 | 99.2 | 98.8 | 98.8 |
|  | Tert-BAM (mass ppm) | 1200 | 800 | 800 | 1200 | 2000 | 1800 |

(In Table, X indicates deviation from the requirement of the present invention.)

Invention of Third Embodiment

The present invention of the third embodiment is described specifically below by way of Examples. The concentration shown in each Example is a concentration quantitatively determined by HPLC.

HPLC condition: high performance liquid chromatograph produced by Waters
Column: X-bridge Shield RP 18 [column size: 4.6 mm (inner diameter)×150 mm (length)], a product of Waters
Elutant: 0.03 mass % aqueous trifluoroacetic acid solution/acetonitrile (90/10 by volume)
Flow rate of elutant: 0.8 ml/min
Detection wavelength: 200 nm The viscosity of copolymer shown in each Example is the actually measured viscosity of a copolymer of ATBS and acrylamide produced by the following method.

An experiment was conducted according to the following procedure. First, 40 g of ATBS was dissolved in 60 g of water. Thereto was added a 48 mass % aqueous NaOH solution for pH adjustment to 8. Thereto was added water to control the concentration of ATBS at 35 mass %. 55.6 g of a 40 mass % aqueous acrylamide solution was added, followed by addition of 5.2 g of water, to control the concentration of monomers at 35 mass %. Nitrogen was blown into the resulting aqueous monomers solution and the solution temperature was controlled at 30° C. Then, there were added 0.7 g of ammonium persulfate, 0.7 g of sodium sulfite, 0.6 g of an aqueous copper chloride solution containing 10 mass ppm of copper ion, and 0.7 g of an aqueous solution containing 10 mass % of V-50 (trade name, a product of Wako Pure Chemical Industries, Ltd.) as a diazo type radical polymerization initiator. A reaction was complete in 2 hours and then a copolymer was taken out.

1.15 g of this copolymer was dissolved in 393 g of water. 23.4 g of sodium chloride was added to obtain a sample solution for viscosity measurement (copolymer concentration: 0.25 mass %). Viscosity measurement was conducted under the following conditions.

Viscometer: Digital viscometer (a product of Brookfield)
Rotor revolution: 60 rpm
Measurement temperature: 25° C.

Example 10

ATBS was produced using a continuous production equipment shown in FIG. 7. In FIG. 7, 100 is a continuous production equipment for ATBS. 2 is a first reaction vessel provided with a stirring device not shown and is covered outside with a jacket 4. Into the jacket 4 is fed a temperature-controlling fluid from a first temperature controller 6. The temperature inside the first reaction vessel 2 is controlled by the temperature-controlling fluid. Into the first reaction vessel 2 are continuously fed acrylonitrile 8 and fuming sulfuric acid 10. Acrylonitrile 8 and fuming sulfuric acid 10 are stirred by the stirring device not shown. This stirring produces a mixed fluid thereof continuously. In this stirring, the water containing acrylonitrile reacts with the sulfur trioxide containing fuming sulfuric acid and becomes sulfuric acid, whereby the water is removed.

The mixed fluid produced in the first reaction vessel 2 is sent to a second reaction vessel 12. A jacket 14 is formed on the outer surface of the second reaction vessel 12. The temperature inside the second reaction vessel 12 is controlled by a temperature-controlling fluid sent to the jacket 14 from a second temperature-controller 16.

Isobutylene 18 is fed into the mixed fluid sent into the second reaction vessel. Inside the second reaction vessel 12, the mixed fluid sent from the first reaction vessel 2 is reacted with isobutylene to form ATBS. This ATBS is suspended in the acrylonitrile fed in excess and acting also as a solvent. As a result, a slurry of ATBS is formed. This slurry is taken outside continuously through a taking-out pipe 20 fitted to the second reaction vessel 12. The slurry taken out is sent to a third step not shown and subjected to solid-liquid separation therein. The cake obtained by the solid-liquid separation is washed with acrylonitrile.

Then, the washed cake is heated and dried in a fourth step. The ATBS cake of the present invention produced as above was analyzed by HPLC to determine its IBSA concentration. The result is shown in Table 5.

Examples 11 to 13

An operation was conducted in the same manner as in Example 10 except that the conditions shown in Table 5 were used. The result is shown in Table 5.

Comparative Examples 4 to 8

An operation was conducted in the same manner as in Example 9 except that the conditions shown in Table 6 were used. The result is shown in Table 6.

TABLE 5

|  |  | Example 10 | Example 11 | Example 12 | Example 13 |
|---|---|---|---|---|---|
| First step | Excessive amount of $SO_3$ (%) | 0.6 | 0.2 | 0.2 | 0.2 |
|  | Residence time (min) | 90 | 90 | 180 | 180 |
|  | Temperature (° C.) | −15 | −15 | −15 | −5 |

TABLE 5-continued

|  |  | Example 10 | Example 11 | Example 12 | Example 13 |
|---|---|---|---|---|---|
| Second step | Residence time (min) | 120 | 120 | 100 | 120 |
|  | Temperature (° C.) | 45 | 45 | 45 | 60 |
|  | IBSA (mass ppm) | 10000 | 9000 | 6000 | 7000 |
| Third step | AN ratio (mass times) | 2 | 2 | 2 | 3 |
|  | IBSA (mass ppm) | 100 | 80 | 60 | 60 |
| Fourth step | Drying temperature (° C.) | 130 | 110 | 110 | 85 |
|  | Drying time (min) | 90 | 180 | 90 | 30 |
|  | IBSA (mass ppm) | 20 | 30 | 20 | 30 |
|  | UL viscosity (mPa · s) | 3.6 | 3.5 | 3.6 | 3.5 |

AN: acrylonitrile

TABLE 6

|  |  | Comp. Example 4 | Comp. Example 5 | Comp. Example 6 | Comp. Example 7 | Comp. Example 8 |
|---|---|---|---|---|---|---|
| First step | Excessive amount of SO$_3$ (%) | 0.6 | 0.2 | 0.6 | 0.6 | 0.6 |
|  | Residence time (min) | 60 X | 80 X | 90 | 90 | 90 |
|  | Temperature (° C.) | −15 | −15 | −15 | −15 | −15 |
| Second step | Residence time (min) | 120 | 120 | 120 | 120 | 120 |
|  | Temperature (° C.) | 45 | 45 | 45 | 45 | 45 |
|  | IBSA (mass ppm) | 15000 | 12000 | 10000 | 10000 | 10000 |
| Third step | AN ratio (mass times) | 2 | 2 | 2 | 1.5 X | 2 |
|  | IBSA (mass ppm) | 150 | 150 | 100 | 180 | 100 |
| Fourth step | Drying temperature (° C.) | 80 | 130 | 60 X | 90 | 80 |
|  | Drying time (min) | 90 | 90 | 90 | 90 | 20 X |
|  | IBSA (mass ppm) | 100 | 40 | 90 | 100 | 80 |
|  | UL viscosity (mPa · s) | 3.0 | 3.4 | 3.0 | 3.0 | 3.1 |

(Note: In Table, X indicates deviation from the requirement of the present invention.)

The invention claimed is:

1. A process for producing 2-acrylamide-2-methylpropanesulfonic acid, which comprises reacting acrylonitrile, fuming sulfuric acid and isobutylene, wherein the concentration of the 2-methyl-2-propenyl-1-sulfonic acid and/or 2-methylidene-1,3-propylenedisulfonic acid present in the reaction system is determined during the reaction and, when the concentration of 2-methyl-2-propenyl-1-sulfonic acid exceeds 12,000 mass ppm and/or the concentration of 2-methylidene-1,3-propylenedisulfonic acid exceeds 6,000 mass ppm, the reaction time is increased to reduce the concentration of sulfur trioxide in the reaction system.

2. A process for producing 2-acrylamide-2-methylpropanesulfonic acid continuously, which comprises reacting acrylonitrile, fuming sulfuric acid and isobutylene, wherein acrylonitrile, fuming sulfuric acid and isobutylene are fed into the reaction system continuously and reacted, the concentration of the 2-methyl-2-propenyl-1-sulfonic acid and/or 2-methylidene-1,3-propylenedisulfonic acid present in the reaction system is determined during the reaction and, when the concentration of 2-methyl-2-propenyl-1-sulfonic acid exceeds 12,000 mass ppm and/or the concentration of 2-methylidene-1,3-propylenedisulfonic acid exceeds 6,000 mass ppm, the amount of sulfur trioxide fed into the reaction system together with sulfuric acid is decreased or the feed of sulfur trioxide is stopped to reduce the concentration of sulfur trioxide in the reaction system.

3. A process for producing 2-acrylamide-2-methylpropanesulfonic acid continuously, which comprises reacting acrylonitrile, fuming sulfuric acid and isobutylene, wherein acrylonitrile, fuming sulfuric acid and isobutylene are fed into the reaction system continuously and reacted, the concentration of the 2-methyl-2-propenyl-1-sulfonic acid and/or 2-methylidene-1,3-propylenedisulfonic acid present in the reaction system is determined during the reaction and, when the concentration of 2-methyl-2-propenyl-1-sulfonic acid exceeds 12,000 mass ppm and/or the concentration of 2-methylidene-1,3-propylenedisulfonic acid exceeds 6,000 mass ppm, the reaction time is increased to reduce the concentration of sulfur trioxide in the reaction system.

4. A process for producing 2-acrylamide-2-methylpropanesulfonic acid, which comprises separating, by filtration, a crude 2-acrylamide-2-methylpropanesulfonic acid from the slurry obtained in the production process according to claim 1, to obtain a cake, and then washing the cake using a solvent selected from the group consisting of acrylonitrile, acetonitrile, acetone, methanol, ethanol, 2-propanol, butanol, ethyl acetate and acetic acid or a mixed solvent thereof.

5. A process for producing 2-acrylamide-2-methylpropanesulfonic acid, which comprises separating, by filtration, a crude 2-acrylamide-2-methylpropanesulfonic acid from the slurry obtained in the production process according to claim 1, to obtain a cake, and then drying the cake at 60 to 130° C. for 10 to 300 minutes.

6. A process for continuously producing 2-acrylamide-2-methylpropanesulfonic acid represented by the following formula (3),

[Formula 20]

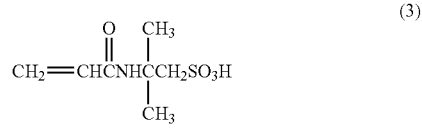

(3)

which comprises mixing acrylonitrile with fuming sulfuric acid in a first reaction vessel to obtain a mixture, feeding the mixture obtained in the first reaction vessel, into a second reaction vessel, reacting there the mixture with isobutylene, and taking out the resulting slurry from the second reaction vessel, wherein, when, in the taken-out slurry, the concentration of 2-methyl-2-propenyl-1-sulfonic acid represented by the following formula (1)

[Formula 21]

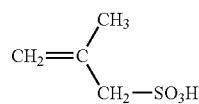

(1)

exceeds 12,000 mass ppm or the concentration of tert-butylacrylamide represented by the following formula (4)

[Formula 22]

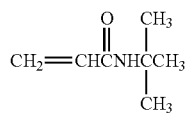

(4)

exceeds 10,000 ppm, the residence time of the mixture of acrylonitrile and fuming sulfuric acid in the first reaction vessel is increased to reduce the concentration of sulfur trioxide in the reaction system.

7. A process for producing 2-acrylamide-2-methylpropanesulfonic acid, which comprises separating, by filtration, a crude 2-acrylamide-2-methylpropanesulfonic acid from the slurry obtained in the production process according to claim 6, to obtain a cake, and then washing the cake using a solvent selected from the group consisting of acrylonitrile, acetonitrile, acetone, methanol, ethanol, 2-propanol, butanol, ethyl acetate and acetic acid or a mixed solvent thereof.

8. A process for producing 2-acrylamide-2-methylpropanesulfonic acid containing 2-methyl-2-propenyl-1-sulfonic acid at 30 mass ppm or lower, which comprises the following first to forth steps:

a first step of mixing fuming sulfuric acid with acrylonitrile of 7 to 30 moles relative to 1 mole of fuming sulfuric acid, for 90 minutes or longer, to produce a mixture of acrylonitrile and fuming sulfuric acid, a second step of contacting the mixture produced in the first step, with isobutylene at 40 to 70° C. for 90 to 180 minutes, to obtain an acrylonitrile slurry of 2-acrylamide-2-methylpropanesulfonic acid represented by the following formula (3)

[Formula 23]

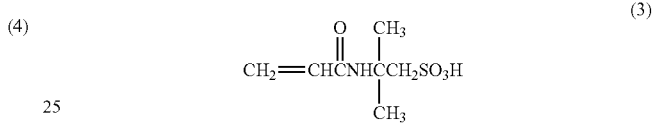

(3)

a third step of subjecting the slurry obtained in the second step, to solid-liquid separation to obtain a cake of crude 2-acrylamide-2-methylpropanesulfonic acid, and then washing the cake with acrylonitrile of mass of at least two times that of the cake, and a fourth step of drying the cake washed in the third step, at 80 to 130° C. for 30 to 300 minutes.

* * * * *